United States Patent [19]

Joseph

[11] 4,248,238

[45] Feb. 3, 1981

[54] HEART STIMULATING APPARATUS

[76] Inventor: Simon P. Joseph, 3 Lowther Rd., Barnes, London, S.W.13, England

[21] Appl. No.: 24,013

[22] Filed: Mar. 26, 1979

[51] Int. Cl.³ ............................................. A61N 1/36
[52] U.S. Cl. ............................................. 128/419 PG
[58] Field of Search ...................... 128/419 PG, 419 P

[56] References Cited

U.S. PATENT DOCUMENTS

| | | | |
|---|---|---|---|
| 3,253,595 | 5/1966 | Murphy, Jr. et al. | 128/419 PG |
| 3,311,111 | 3/1967 | Bowers | 128/419 PG |
| 3,433,228 | 3/1969 | Keller, Jr. | 128/419 PG |
| 3,648,707 | 3/1972 | Great Batch | 128/419 PG |
| 3,866,614 | 2/1975 | Svensson | 128/419 PG |

*Primary Examiner*—William E. Kamm
*Attorney, Agent, or Firm*—Leydig, Voit, Osann, Mayer & Holt, Ltd.

[57] ABSTRACT

The invention relates to heart stimulation apparatus.

It is possible to stimulate the heart in one of the atria or one of the ventricles and the invention concerns implantation of two electrodes (which may both be in the same location) and the provision of means for changing over the operative electrode either automatically or at will.

The invention is applicable to the stimulation of hearts which do not otherwise operate with a steady beat.

8 Claims, 5 Drawing Figures

FIG 2 TRIPLE MODE PACEMAKER

HEART STIMULATING APPARATUS

This invention relates to apparatus for stimulating the activity of the heart, such apparatus being known generally as "Pacemakers" and will be referred to herein by that term.

The normal sequence of electrical activation of the heart begins from the sino-atrial (SA) node in the high right atrium (RA); the electrical impulses traverse the atria to reach the specialised atrio-ventricular (AV) conduction system of the heart through which they pass to reach the ventricles. This sequence results in atrial stimulation causing atrial contraction followed 120-200 msec later by ventricular stimulation causing ventricular contraction. The two main pathologies which disturb this sequence are atrio-ventricular (AV) block when the impulse fails to reach the ventricles which then beat at their own intrinsically slow and unreliable rate, and SA node disease which causes a defect in initial impulse formation and hence a slow and unreliable beating of the whole heart. These two pathologies, which can co-exist, may cause partial or complete loss of consciousness and sudden death. They are treated by the connection of an artificial pulse generator (usually called a "pacemaker") to the heart by means of an electrode (or 'electrode catheter') sutured to the outside of the heart or passed to the inside via a vein (transvenous).

Pacemakers as currently in use may include an electrode which serves to stimulate the atrium or an electrode to stimulate the ventricle of a heart.

Alternatively, it has been proposed to use both atrial and ventricular electrodes sequentially.

Cardiac pacing is, at present, usually accomplished by a ventricular stimulation electrode in order to overcome an atrio-ventricular block. Conveniently, the pacemaker is connected through a catheter electrode to one of the ventricles of the heart. It has also been proposed, alternatively, to treat sinus node disease in the absence of any atrio-ventricular block, by stimulating one of the atria via a catheter electrode. The latter mode has the advantage of retaining both atrial-contraction and physiological ventricular contraction with increased cardiac performance but it has two main disadvantages:

1. The catheter electrode position in the atrium is mechanically less stable when the transvenous route is used for the catheter than in the ventricular;
2. The patient with SA node disease may progress to acquire AV conduction disease with concomitant loss of ventricular stimulation. Because of these disadvantages atrial pacing has not been widely practised. A disturbance in the position or function of the atrial electrode may prevent the stimulus from activating the atrium; this is known as atrial exit block. The effect of cardiac pacing is then lost; similarly the onset of AV conduction disease may prevent the stimulus from activating the ventricles with loss of ventricular contraction. In these circumstances there is a need to change from atrial pacing via the atrial electrode to ventricular pacing via a ventricular electrode. With the development of these complications it would be necessary to change the part of the heart to be stimulated. If the electrodes are implanted surgically such a changeover requires a major operation and even if the catheter carrying the electrode is initially inserted transvenously, some disturbance is involved and particularly under circumstances where a changeover might become necessary the disturbance is particularly undesirable.

According to the present invention there is provided heart pacing apparatus comprising first and second electrodes, switching means to select either electrode for controlling the apparatus, means for supplying electrical pulses to the electrodes and means for sensing the potential at either one or the other of the electrodes, characterized in that the switching means are also operative to changeover stimulation from one electrode to the other in dependence upon signals received from the sensing means.

Three pacemakers embodying the invention will now be described, by way of example, with reference to the accompanying diagrammatic drawings, in which.

The invention is applicable to pacemakers implanted both surgically and by the use of a catheter placed in the heart transvenously. Again, the invention can be applied to a variety of different circuits and those illustrated in the accompanying drawings are not exhaustive of the possible circuits to which the invention is applicable.

As is conventional the pacemaker may have a unipolar electrode in the heart with the other electrode on the outside of the pacemaker casing. Alternatively, both electrodes may be at the end of a catheter. The invention is applicable to both electrode systems.

Figure 1:
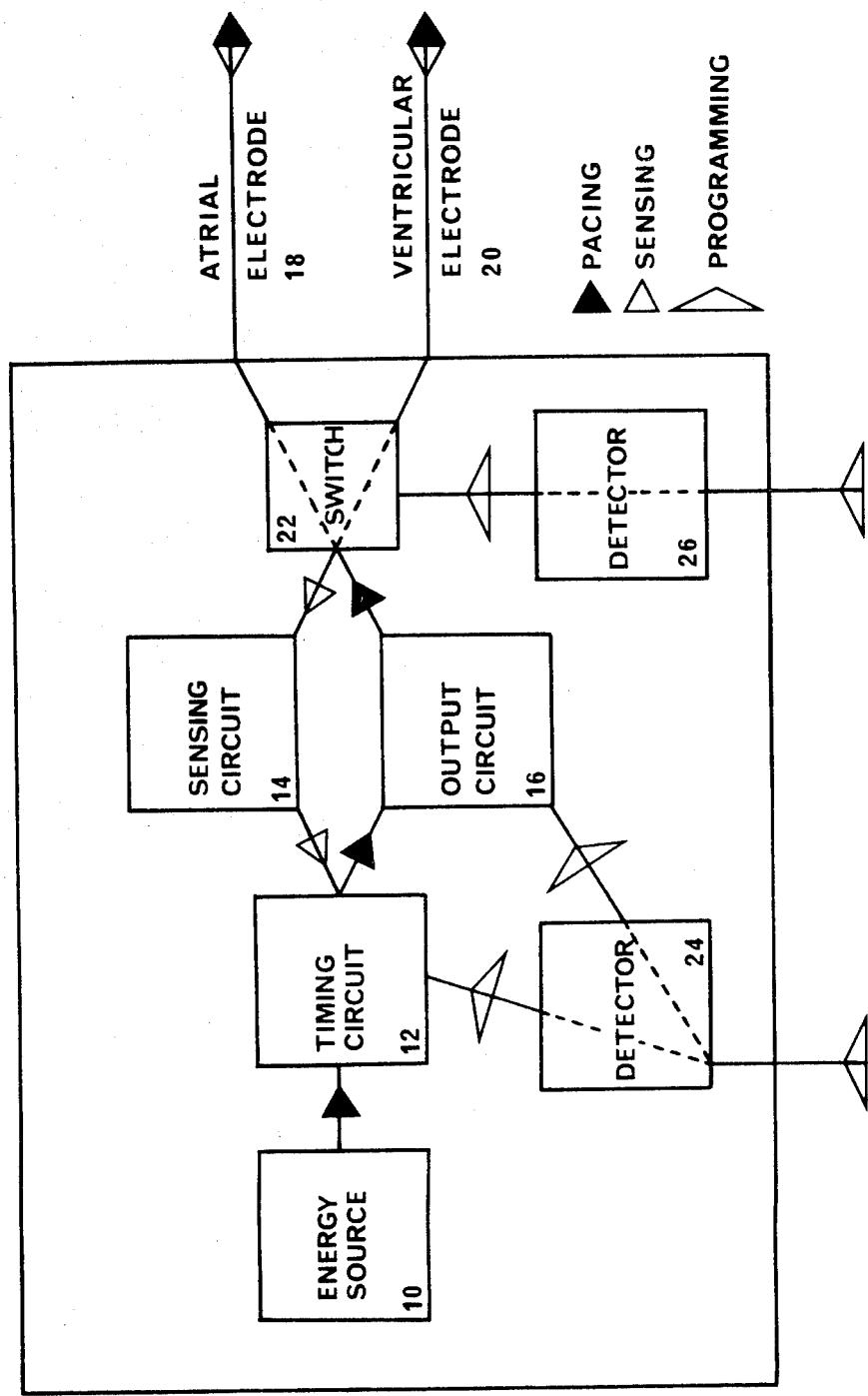
FIG. 1 is a diagram of a dual pacemaker in accordance with the invention.

Referring now to the drawings and in particular to FIG. 1, the pacemaker comprises an energy source 10 for example a mercury-zinc or a lithium based cell, connected to a timing circuit 12 which is arranged to receive messages from a sensing circuit 14 and to deliver an output to an output circuit 16 which supplies electrical pulses selectively either to an atrial electrode 18 or to a ventricular electrode 20 through a switch 22. The sensing circuit receives a feed-back from the atrial or ventricular electrode 18,22.

Optionally a detector circuit 24 for detecting external programming may be connected to the timing circuit 12 or to the output circuit 16. This external programming enables changes of frequency, amplitude or width of the pulses supplied to the electrode. The energy source, the timing, output, sensing, programming, and detector circuits are all conventional.

The sensing circuit 14 detects intrinsic cardiac electrical activity through the catheter electrode 18,20 which is normally the same as the electrode which carries the pacing pulses. When the intrinsic cardiac activity exceeds a predetermined rate, the amplified signal from the heart either blocks or triggers, as appropriate, the timing circuit 12, thus inhibiting pacemaker activity or stimulating it to fire synchronously, and thus ineffectively, with the heart's own pulses.

The switch device 22 may be electronic, for example a semi-conductor switch, or may be electro-mechanical but should have a low resistance whichever switch is selected. Such a switch can be actuated by a static or pulsating magnetic field from externally of the patient's body through a detector circuit 26. Once the switching operation has been carried out the switch will remain in the same position until subjected to another magnetic field when this is required.

In an alternative unillustrated construction, if a reed switch is incorporated, electrical pulses are fed to a detector, a counter and a decoder which will operate the switch 22.

As will be apparent from FIG. 1, the output and sensing circuits 14, 16, of the pacemaker are connected to one of the two electrodes 18, 20 through the switch 22 and this enables both sensing and pacing to be effected through either electrode and further this allows for atrial pacing and sensing or alternatively ventricular pacing and sensing.

Figure 2:
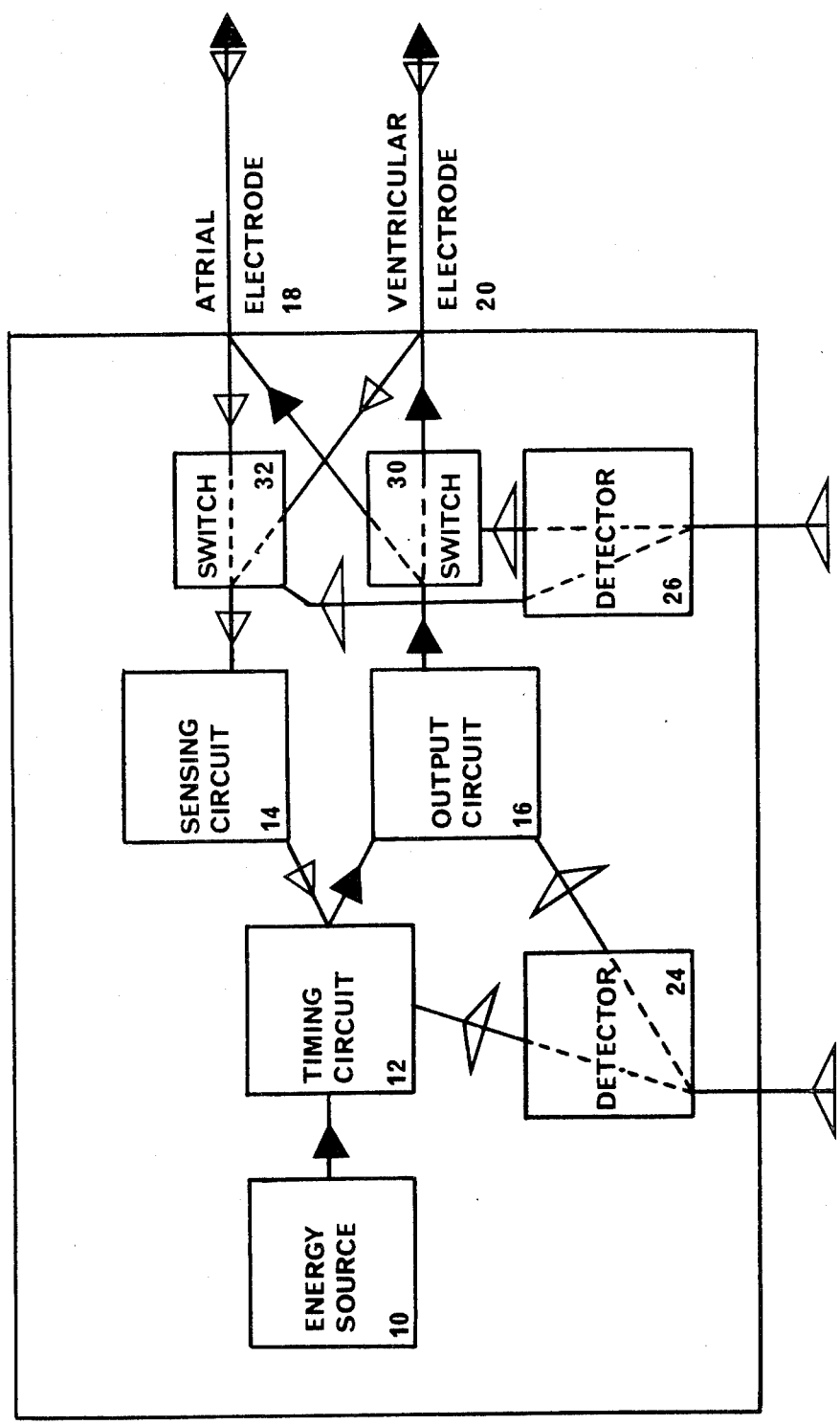
FIG. 2 is a diagram of a triple mode pacemaker in accordance with the invention.

In the modification illustrated in FIG. 2, the basic circuits are the same as in the first embodiment and are given the same reference numerals, but two switches 30, 32 are incorporated, one of which 30 determines the electrode 18, 20 to be connected to the output circuit 16 of the pacemaker and the other 32 of which determines the electrode connected to the sensing circuit 14 of the pacemaker. It follows that one electrode can be used for sensing and the other for pacing. The circuit of FIG. 2 thus allows for a third mode, namely ventricular sensing and atrial pacing which could be used in the event that atrial sensing fails but atrial pacing is retained. The circuit also gives a fourth possible mode, namely atrial sensing and ventricular pacing but this is undesirable physiologically and would be avoided by appropriate blocking circuitry or incorporation of an appropriate cut-out circuit in a programming device.

By the use of either of the hereinbefore described pacemakers embodying the invention, some of the disadvantages of atrial stimulation are believed to be circumvented. In particular, although pacemakers embodying the invention as described with reference to FIG. 2 are intended to achieve atrial pacing with its attendant advantages, in the event that atrial sensing fails, the switch can be operated to allow ventricular pacing and further in the event that both atrial sensing and pacing fail, the switch means can be operated to allow both ventricular sensing and pacing.

Figure 3:
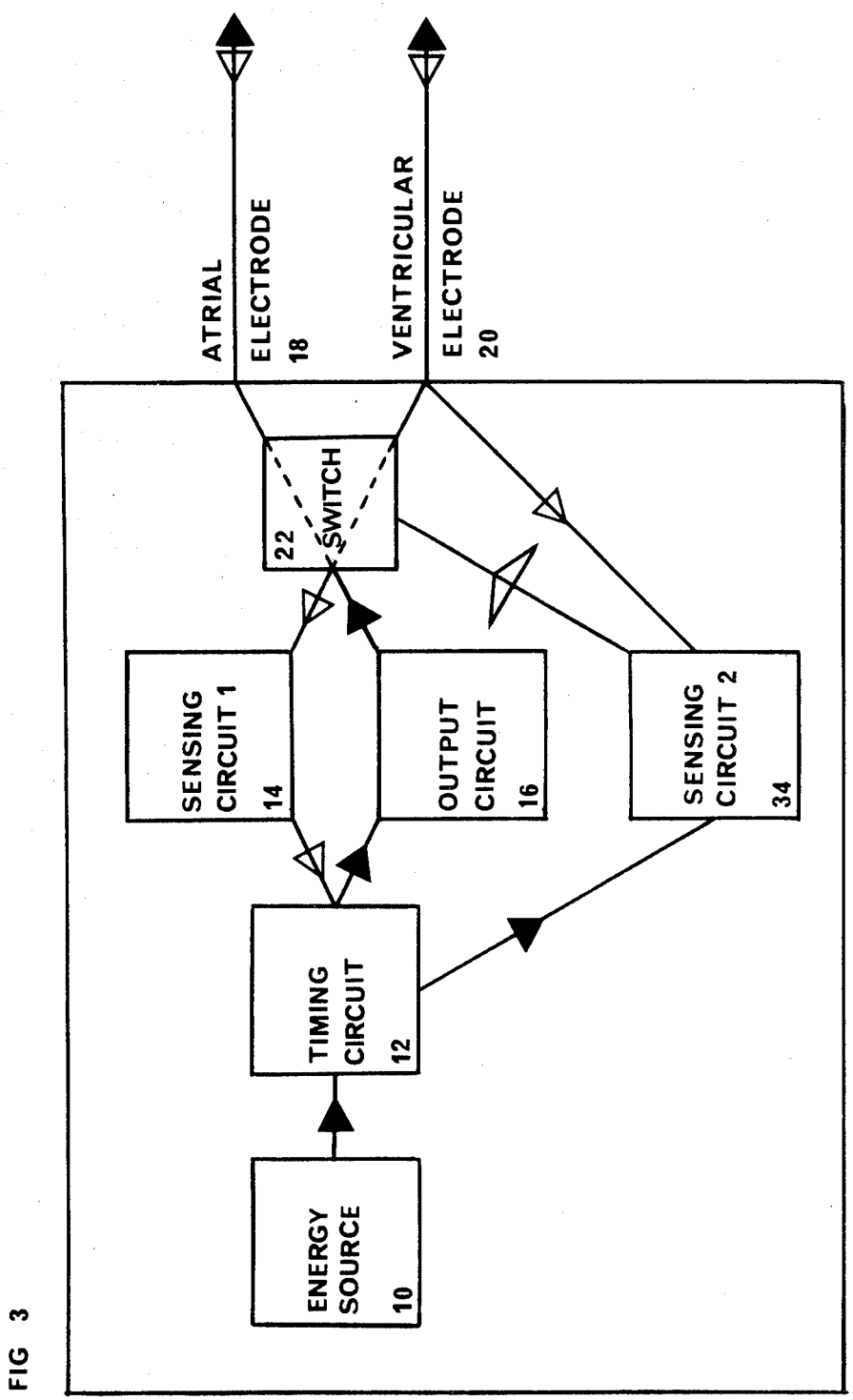
FIG. 3 is a diagram of another embodiment of pacemaker.
Figure 4:
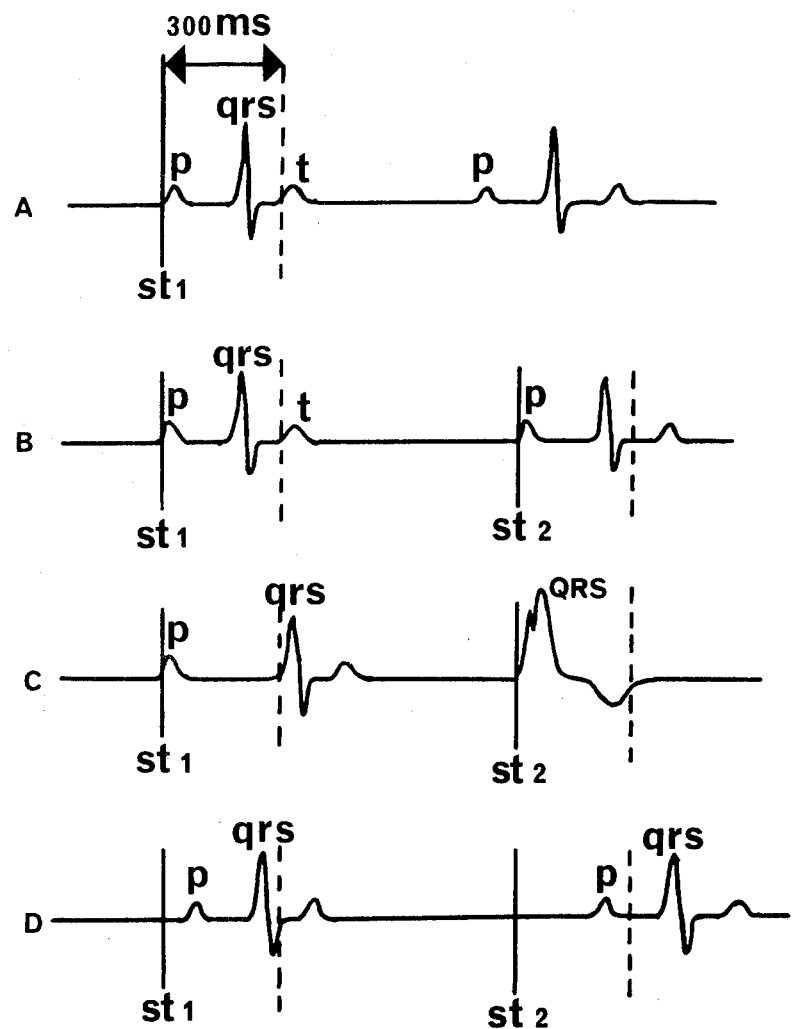
FIG. 4 is a series of electrocardiographic diagrams.

Reference will now be made to FIGS. 3 and 4. The output terminal switching may be arranged to occur automatically by the provision of an additional circuit within the pacemaker so providing an additional safeguard for the patient. This may be in addition to the external programming means described with reference to FIGS. 1 and 2.

An additional sensing circuit 34 is incorporated in the pacemaker (FIG. 3) which receives an input from the timing circuit 12 and from the ventricular electrode 20 and is capable of delivering an output to the switch 22. The switch is activated on receipt of a signal from the timing circuit 12 and is disabled on receipt of a signal from the ventricular electrode 20 at any time in the subsequent 300 msec. If no signal is received from the ventricular electrode 20 within 300 msec after activation it emits a signal which activates switch 22 changing the output from the output circuit (16) from the atrial 18 to the ventricular electrode 20.

This sequence will be explained further with reference to FIG. 4 which represents the electrocardiogram in various paced and unpaced modes. "St" represents pacemaker stimuli, 'p' represents spontaneous or paced atrial activation 'qrs' represents ventricular activation following normal AV conduction and 'QRS' represents ventricular activation after ventricular pacing.

In A the initial beat is an atrial paced beat p followed by normal AV conduction and ventricular qrs activation. The second beat is spontaneous and occurs within the escape period of the demand pacemaker the output of which is inhibited according to known methods.

In B both beats follow atrial pacing and normal AV conduction.

In C the initial atrially paced beat p is followed by delayed AV conduction and ventricular qrs activation occurs more than 300 msec after St1; sensing circuit 34 therefore switches the output of the pacer to the ventricular electrode and St2 is followed by ventricular activation.

In D there is atrial exit block and St1 is not followed by atrial activation. Although spontaneous atrial activation p is followed by ventricular contraction qrs within 300 msec of St1, after the second stimulus (St2) the activation qrs falls outside the 300 msec period, and the output of the pacemaker would be switched to the ventricular electrode for the third beat. Thus in the event of AV conduction delay or block C or atrial exit block D after atrial pacing the pacer output is switched to the ventricular electrode.

Should AV conduction delay or block occur whilst the spontaneous atrial beat p rate is in excess of the demand rate of the pacemaker, which will therefore be in the inhibited, demand mode, the sensing circuit 30 will receive no activation from the timing circuit 12 and will not activate switch 22.

Figure 5:
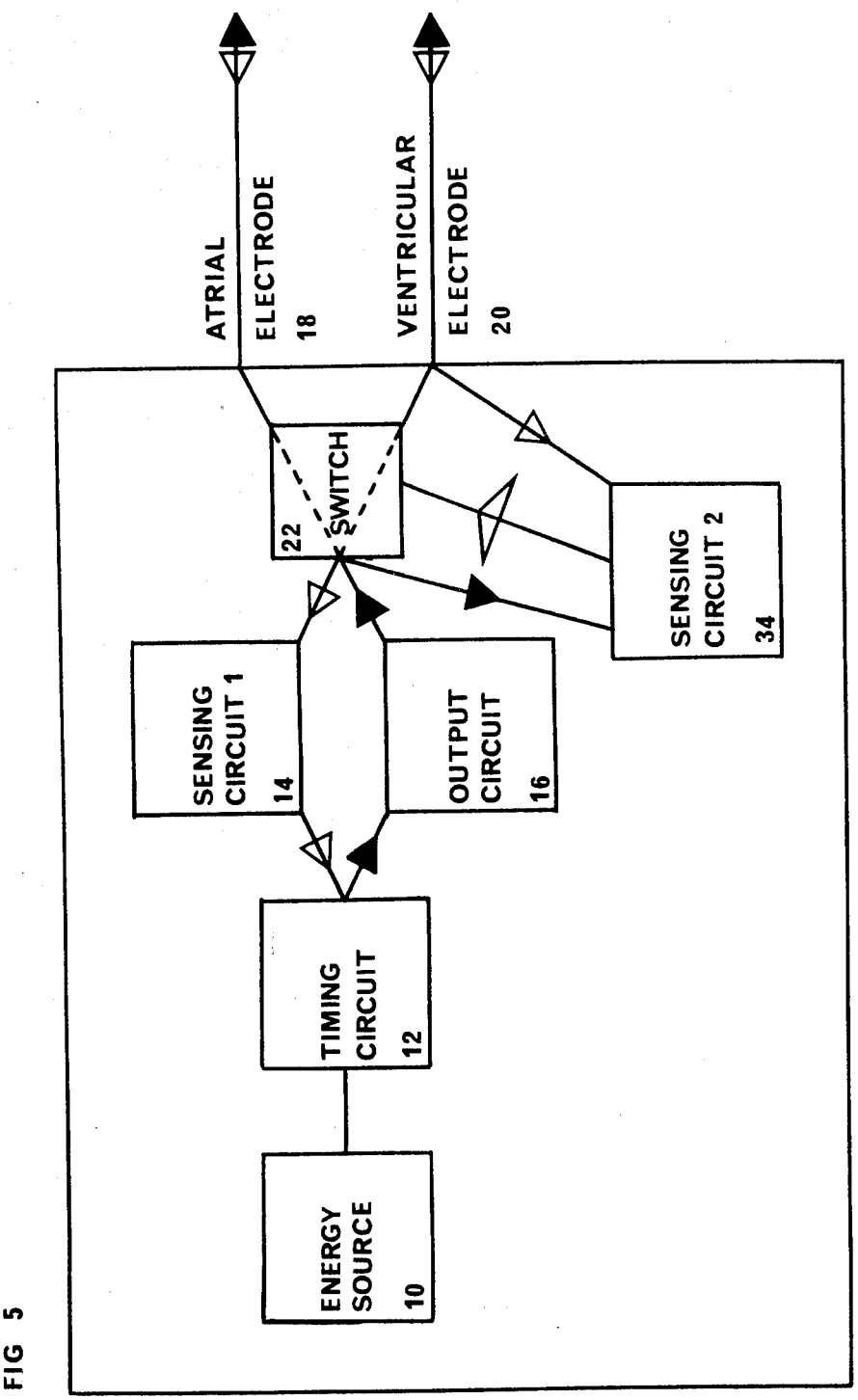
FIG. 5 is a diagram of a modification of the embodiment of FIG. 3.

This may be prevented by a further arrangement illustrated in FIG. 5 in which the sensing circuit 31 receives its actuating signal from the proximal (internal) side of the switch 22. The sensing circuit 34 would then activate switch 22 if the 'qrs' signal from ventricular electrode 20 fell more than 300 msec beyond either a signal from output circuit 16 or a 'p' wave which traversed the switch 22 from the atrial electrode 18.

After activation of switch 22 to transmit and deliver signal from ventricular electrode 20 and in order to prevent a reversion from ventricular pacing via ventricular electrode 20 to atrial pacing via atrial electrode 18, which might occur due to triggering of the sensing circuit 34 via a 'qrs' activation transmitted from ventricular electrode 20 through switch 22, an additional blocking circuit could be inserted between sensing circuit 34 and switch 22, such that the switch 22 could only be activated from sensing circuit 34 once, although external programming by means of detector circuit 26 in FIGS. 1 and 2 could still effect further activation of switch 22.

Similar circuitry for automatic switching of output terminal, to that outlined above could apply not only to the arrangement in FIG. 1 whereby input and output terminals are controlled by a single switch 22 (FIG. 1) but also where input and output (sensing and pacing) are controlled by two switches 30 and 32—FIG. 2.

Although these programmable output and input terminal pacemakers are intended primarily to allow the safe institution of atrial pacing with the ability to change from atrial to ventricular pacing without the need for surgical intervention in the event of the problems outlined above associated with atrial pacing, these pacemakers may also have additional applications. They would for example allow the connection of the pacemaker by two electrodes to the same part of the heart such as two ventricular electrodes, each electrode being conventional, allowing duplication of the electrode. This would be advantageous because at the present time, when more long-lasting energy sources are being developed, it is the electrodes which have become the limiting feature of the pacemaker system; after a period of several years the electrodes are liable to fracture requiring surgical intervention even though the energy source has not become exhausted. Indeed it is common practice, when the electrodes are sutured to the outside of the heart by means of a major surgical procedure, to attach two electrodes, the second of which is normally 'capped' and left lying loose in the event of future need.

By means of a programmable output terminal pacemakers herein described both electrodes could be attached and in the event of failure of one electrode from whatever cause, the second could be used without surgical intervention. An alternative use would be for testing experimental electrodes. A variety of experimental and new electrodes is appearing at the present time and more are likely to be developed in the future. Although they are always tested first in the experimental animal, there is always an ethical problem with initial application in the human. The use of a programmable output terminal pacemaker would allow ethically acceptable use of such an experimental electrode together with a conventional electrode, thus allowing change from experimental to conventional electrode should the former fail from whatever cause.

I claim:

1. In heart-pacing apparatus
   a first electrode implanted in a heart,
   a second electrode implanted in a heart,
   switching means operative to select either the first or the second electrode for controlling the apparatus,
   means electrically connecting the switching means and the first and second electrodes,
   means for supplying electrical pulses to the electrodes through the switching means and the electrical connection means,
   means for sensing the potential at either the first or the second electrode through the electrical connection means and the switching means, and
   further electrical connection means between the sensing means, the pulse supply means and the electrodes by which signals from the sensing means are operative to change over heart stimulation from one electrode to the other.

2. Apparatus according to claim 1 wherein the first electrode serves to stimulate one of the atria of the heart and the second electrode serves to stimulate one of the ventricles of the heart, and the switching means is controllable from externally of the body.

3. Apparatus according to claim 2, wherein the switching means comprises two switches, one of which determines the electrode to be connected to the pulse-supplying means of the apparatus and the other of which determines the electrode to be connected to the sensing of the apparatus.

4. Apparatus according to claim 1 wherein the first electrode serves to stimulate one of the chambers of the heart and the second electrode serves to stimulate the same chamber, both said electrodes being connected in the circuit of the sensing means through the electrical connection means and the switching means.

5. Apparatus according to claim 1, wherein the switching means is a semi-conductor switch of low resistance, and the apparatus further includes a detector, a counter and a decoder connected by the electrical connections to operate the semi-conductor switch.

6. Apparatus according to claim 1 comprising second sensing means serving to sense feed-back from one of the said electrodes and arranged automatically to change-over the pacing action from one electrode to the other in the event of absence of a signal from said one electrode.

7. Apparatus according to claim 1, wherein the sensing means comprises a first sensing circuit connected through the switching means and the electrical connection means to receive a feed-back signal from one of the electrodes and to supply an output to the electrical pulse supply means, said pulse supply means including a timing circuit and an output circuit connected to receive pulses from the timing circuit and to supply one of the electrodes through the electrical connection means and the switching means and the apparatus further includes a second sensing circuit connected to control the switching means to change-over automatically the pacing mode.

8. In heart-pacing apparatus
   an energy source,
   a first electrode implanted in a heart for atrial stimulation thereof,
   a second electrode implanted in a heart for ventricular stimulation thereof;
   switching means operative to select either the first or the second electrode for controlling the apparatus,
   means electrically connecting the switching means and the first and second electrodes for transmitting signals to the electrodes and receiving signals from them,
   means for supplying, in any given operative state, electrical pulses to one of the electrodes through the switching means and the electrical connection means,
   means for sensing the potential at either the first or the second electrode through the electrical connection means and the switching means, and
   further electrical connection means between the sensing means, the pulse supply means and the electrodes by which signals from the sensing means are operative to change over stimulation from the atrial electrode to the ventricular electrode and vice versa.

* * * * *